(12) United States Patent
Dugan

(10) Patent No.: US 10,486,067 B2
(45) Date of Patent: Nov. 26, 2019

(54) SYSTEMS AND METHODS FOR FITNESS AND VIDEO GAMES

(71) Applicant: Brian M. Dugan, Sleepy Hollow, NY (US)

(72) Inventor: Brian M. Dugan, Sleepy Hollow, NY (US)

( * ) Notice: Subject to any disclaimer, the term of this patent is extended or adjusted under 35 U.S.C. 154(b) by 0 days.

(21) Appl. No.: 15/907,261

(22) Filed: Feb. 27, 2018

(65) Prior Publication Data

US 2018/0185754 A1     Jul. 5, 2018

Related U.S. Application Data

(63) Continuation of application No. 15/364,241, filed on Nov. 29, 2016, now Pat. No. 9,914,053, which is a (Continued)

(51) Int. Cl.
*A63F 13/42* (2014.01)
*A63F 13/428* (2014.01)
(Continued)

(52) U.S. Cl.
CPC ........ *A63F 13/428* (2014.09); *A63B 24/0062* (2013.01); *A63B 24/0084* (2013.01); *A63B 71/0622* (2013.01); *A63F 13/211* (2014.09); *A63F 13/216* (2014.09); *A63F 13/31* (2014.09); *A63F 13/795* (2014.09); *A63F 13/816* (2014.09); *A63B 2071/0647* (2013.01); *A63B 2225/20* (2013.01); *A63F 13/332* (2014.09); *A63F 2300/204* (2013.01); *A63F 2300/556* (2013.01); *A63F 2300/5573* (2013.01);
(Continued)

(58) Field of Classification Search
CPC ...... G06F 19/3481; A63F 13/42; A63F 13/00; A63B 24/0021; A63B 24/00
See application file for complete search history.

(56) References Cited

U.S. PATENT DOCUMENTS 3,834,702 A    9/1974   Bliss
4,484,743 A    11/1984  Williams
(Continued)

FOREIGN PATENT DOCUMENTS

EP     1 292 217 B1    11/2005
EP     1 639 939        3/2006
(Continued)

OTHER PUBLICATIONS

Busch, Fritz "Diabetes Institute Brings Dakota, New Ulm Together" Jun. 10, 2001. Ogden Newspapers, Inc.
(Continued)

*Primary Examiner* — Reginald A Renwick
(74) *Attorney, Agent, or Firm* — Dugan & Dugan, PC

(57) ABSTRACT

In some aspects, a system is provided that includes (1) a plurality of mobile devices; and (2) an application on each mobile device, the application adapted to (a) allow exercisers to form an exercise group; (b) track position or change in position of each exerciser in the exerciser group; and (c) display an avatar having a position that is controlled by a position or change in position of one or more member of the exercise group. Numerous other aspects are provided.

18 Claims, 6 Drawing Sheets

Related U.S. Application Data continuation of application No. 13/433,285, filed on Mar. 28, 2012, now Pat. No. 9,533,228.

(60) Provisional application No. 61/468,444, filed on Mar. 28, 2011, provisional application No. 61/472,191, filed on Apr. 5, 2011.

(51) Int. Cl.

| | | |
|---|---|---|
| *A63F 13/816* | (2014.01) | |
| *A63F 13/795* | (2014.01) | |
| *A63F 13/216* | (2014.01) | |
| *A63F 13/211* | (2014.01) | |
| *A63F 13/31* | (2014.01) | |
| *A63B 24/00* | (2006.01) | |
| *A63B 71/06* | (2006.01) | |
| *A63F 13/332* | (2014.01) | |
| *G06F 19/00* | (2018.01) | |
| *G16H 20/60* | (2018.01) | |

(52) U.S. Cl.
CPC .. *A63F 2300/8005* (2013.01); *G06F 19/3481* (2013.01); *G16H 20/60* (2018.01)

(56) References Cited

U.S. PATENT DOCUMENTS

| | | |
|---|---|---|
| 4,542,897 A | 9/1985 | Melton et al. |
| 4,735,410 A | 4/1988 | Nobuta |
| 4,817,938 A | 4/1989 | Nakao et al. |
| 4,858,930 A | 8/1989 | Sato |
| 4,976,435 A | 12/1990 | Shatford et al. |
| 5,001,632 A | 3/1991 | Hall-Tipping |
| 5,142,358 A | 8/1992 | Jason |
| 5,213,555 A | 5/1993 | Hood |
| RE34,728 E | 9/1994 | Hall-Tipping |
| 5,362,069 A | 11/1994 | Hall-Tipping |
| 5,377,100 A | 12/1994 | Pope et al. |
| 5,462,504 A | 10/1995 | Trulaske et al. |
| 5,515,865 A | 5/1996 | Scanlon |
| 5,527,239 A | 6/1996 | Abbondanza |
| 5,591,104 A | 1/1997 | Andrus et al. |
| 5,592,401 A | 1/1997 | Kramer |
| 5,616,078 A | 4/1997 | Oh |
| 5,624,316 A | 4/1997 | Roskowski et al. |
| 5,645,513 A | 7/1997 | Haydocy et al. |
| 5,667,459 A | 9/1997 | Su |
| 5,672,107 A | 9/1997 | Clayman |
| 5,702,323 A | 12/1997 | Poulton |
| 5,781,698 A | 7/1998 | Teller et al. |
| 5,885,156 A | 3/1999 | Toyohara et al. |
| 5,902,250 A | 5/1999 | Verrier et al. |
| 5,918,603 A | 7/1999 | Brown |
| 5,928,133 A | 7/1999 | Halyak |
| 5,947,868 A | 9/1999 | Dugan |
| 5,982,352 A | 11/1999 | Pryor |
| 6,024,675 A | 2/2000 | Kashiwaguchi |
| 6,062,216 A | 5/2000 | Corn |
| 6,066,075 A | 5/2000 | Poulton |
| 6,152,856 A | 11/2000 | Studor et al. |
| 6,179,713 B1 | 1/2001 | James et al. |
| D439,981 S | 4/2001 | Kasabach et al. |
| 6,213,872 B1 | 4/2001 | Harada et al. |
| 6,244,988 B1 | 6/2001 | Delman |
| 6,251,010 B1 | 6/2001 | Tajiri et al. |
| 6,267,677 B1 | 7/2001 | Tajiri et al. |
| 6,302,789 B2 | 10/2001 | Harada et al. |
| D451,604 S | 12/2001 | Kasabach et al. |
| 6,347,993 B1 | 2/2002 | Kondo et al. |
| 6,354,940 B1 | 3/2002 | Itou et al. |
| 6,375,572 B1 | 4/2002 | Masuyama et al. |
| D460,971 S | 7/2002 | Sica et al. |
| 6,456,749 B1 | 9/2002 | Kasabach et al. |
| 6,482,092 B1 | 11/2002 | Tajiri et al. |
| 6,494,830 B1 | 12/2002 | Wessel |
| 6,513,160 B2 | 1/2003 | Dureau |
| 6,514,199 B1 | 2/2003 | Alessandri |
| 6,527,711 B1 | 3/2003 | Stivoric et al. |
| 6,579,231 B1 | 6/2003 | Phipps |
| 6,585,622 B1 | 7/2003 | Shum et al. |
| 6,595,858 B1 | 7/2003 | Tajiri et al. |
| 6,595,929 B2 | 7/2003 | Stivoric et al. |
| 6,605,038 B1 | 8/2003 | Teller et al. |
| 6,628,847 B1 | 9/2003 | Kasabach et al. |
| 6,641,482 B2 | 11/2003 | Masuyama et al. |
| 6,652,383 B1 | 11/2003 | Sonoda et al. |
| 6,705,972 B1 | 3/2004 | Takano et al. |
| 6,720,983 B1 | 4/2004 | Massaro et al. |
| 6,746,371 B1 | 6/2004 | Brown et al. |
| 6,758,746 B1 | 7/2004 | Hunter et al. |
| 6,786,825 B2 | 9/2004 | Kawazu |
| 6,796,927 B2 | 9/2004 | Toyama |
| 6,881,176 B2 | 4/2005 | Oishi et al. |
| 6,888,779 B2 | 5/2005 | Mollicone et al. |
| 6,902,513 B1 | 6/2005 | McClure |
| 6,966,837 B1 | 11/2005 | Best |
| 7,020,508 B2 | 3/2006 | Stivoric et al. |
| 7,041,049 B1 | 5/2006 | Raniere |
| 7,057,551 B1 | 6/2006 | Vogt |
| 7,068,860 B2 | 6/2006 | Kasabach et al. |
| 7,153,262 B2 | 12/2006 | Stivoric et al. |
| 7,261,690 B2 | 8/2007 | Teller et al. |
| 7,285,090 B2 | 10/2007 | Stivoric et al. |
| 7,627,139 B2 | 12/2009 | Marks |
| 7,628,730 B1 | 12/2009 | Watterson et al. |
| 7,684,592 B2 | 3/2010 | Paul |
| 7,749,056 B2 | 7/2010 | Ando et al. |
| 7,874,957 B2 | 1/2011 | Hurwitz |
| 7,931,563 B2 | 4/2011 | Shaw et al. |
| 7,934,983 B1 | 5/2011 | Eisner |
| 7,946,959 B2 | 5/2011 | Shum et al. |
| 8,152,531 B1* | 4/2012 | Puopolo ............... G09B 5/125 434/247 |
| 8,188,868 B2 | 5/2012 | Case, Jr. |
| 8,284,157 B2 | 10/2012 | Markovic et al. |
| 8,287,383 B1 | 10/2012 | Etter et al. |
| 8,287,436 B2 | 10/2012 | Shum et al. |
| 8,292,743 B1 | 10/2012 | Etter et al. |
| 8,313,416 B2 | 11/2012 | Ellis et al. |
| 8,444,491 B2 | 5/2013 | Bethke et al. |
| 8,491,395 B2 | 7/2013 | Auterio et al. |
| 8,496,532 B1 | 7/2013 | Bethke et al. |
| 8,506,409 B2 | 8/2013 | Bethke et al. |
| 8,556,778 B1 | 10/2013 | Dugan |
| 8,608,570 B1 | 12/2013 | Mahajan et al. |
| 8,654,198 B2 | 2/2014 | Pryor |
| 8,784,273 B2 | 7/2014 | Dugan |
| 9,162,142 B2 | 10/2015 | Shum |
| 9,177,387 B2 | 11/2015 | Marks |
| 2002/0022516 A1 | 2/2002 | Forden |
| 2002/0080035 A1 | 6/2002 | Youdenko |
| 2002/0082065 A1 | 6/2002 | Fogel et al. |
| 2002/0082077 A1 | 6/2002 | Johnson et al. |
| 2002/0090985 A1 | 7/2002 | Tochner et al. |
| 2002/0151992 A1 | 10/2002 | Hoffberg et al. |
| 2002/0160883 A1 | 10/2002 | Dugan |
| 2002/0163495 A1 | 11/2002 | Doynov |
| 2003/0224337 A1 | 12/2003 | Shum et al. |
| 2003/0224855 A1 | 12/2003 | Cunningham |
| 2004/0023761 A1 | 2/2004 | Emery |
| 2004/0053690 A1 | 3/2004 | Fogel et al. |
| 2005/0049022 A1 | 3/2005 | Mullen |
| 2005/0068169 A1 | 3/2005 | Copley et al. |
| 2005/0101845 A1 | 5/2005 | Nihtila |
| 2005/0177051 A1 | 8/2005 | Almen |
| 2005/0275541 A1 | 12/2005 | Sengupta et al. |
| 2006/0025282 A1 | 2/2006 | Redmann |
| 2006/0031102 A1 | 2/2006 | Teller et al. |
| 2006/0089543 A1 | 4/2006 | Kim et al. |
| 2006/0122474 A1 | 6/2006 | Teller et al. |
| 2006/0224051 A1 | 10/2006 | Teller et al. |
| 2006/0264730 A1 | 11/2006 | Stivoric et al. |
| 2006/0281543 A1 | 12/2006 | Sutton et al. |

(56) References Cited

U.S. PATENT DOCUMENTS

| | | |
|---|---|---|
| 2007/0004482 A1 | 1/2007 | Ando et al. |
| 2007/0038038 A1 | 2/2007 | Stivoric et al. |
| 2007/0053513 A1 | 3/2007 | Hoffberg |
| 2007/0087828 A1 | 4/2007 | Robertson |
| 2007/0111858 A1 | 5/2007 | Dugan |
| 2007/0167204 A1 | 7/2007 | Lyle et al. |
| 2007/0173705 A1 | 7/2007 | Teller et al. |
| 2007/0197274 A1 | 8/2007 | Dugan |
| 2007/0208233 A1 | 9/2007 | Kovacs |
| 2007/0239479 A1* | 10/2007 | Arrasvuori ............ G06Q 10/10 705/2 |
| 2007/0260482 A1 | 11/2007 | Nurmela et al. |
| 2008/0027337 A1 | 1/2008 | Dugan et al. |
| 2008/0094226 A1 | 4/2008 | O'Shea et al. |
| 2008/0129518 A1 | 6/2008 | Carlton-Foss |
| 2008/0146892 A1 | 6/2008 | LeBoeuf et al. |
| 2008/0158232 A1* | 7/2008 | Shuster ................. G06T 13/40 345/474 |
| 2008/0167861 A1 | 7/2008 | Inoue et al. |
| 2008/0191864 A1 | 8/2008 | Wolfson |
| 2008/0218310 A1 | 9/2008 | Alten et al. |
| 2008/0281633 A1 | 11/2008 | Burdea et al. |
| 2008/0318679 A1 | 12/2008 | Tran et al. |
| 2009/0005140 A1 | 1/2009 | Rose et al. |
| 2009/0121894 A1 | 5/2009 | Wilson et al. |
| 2009/0221338 A1 | 9/2009 | Stewart |
| 2009/0270743 A1 | 10/2009 | Dugan et al. |
| 2010/0033303 A1 | 2/2010 | Dugan et al. |
| 2010/0069148 A1 | 3/2010 | Cargill |
| 2010/0137064 A1 | 6/2010 | Shum |
| 2010/0160041 A1 | 6/2010 | Grant et al. |
| 2010/0240458 A1 | 9/2010 | Gaiba et al. |
| 2010/0287011 A1 | 11/2010 | Muchkaev |
| 2010/0325194 A1* | 12/2010 | Williamson ............ H04W 4/02 709/203 |
| 2011/0065504 A1 | 3/2011 | Dugan et al. |
| 2011/0081973 A1 | 4/2011 | Hall |
| 2011/0082008 A1 | 4/2011 | Cheung et al. |
| 2011/0175801 A1 | 7/2011 | Markovic et al. |
| 2011/0190055 A1 | 8/2011 | Leyvand et al. |
| 2011/0260830 A1 | 10/2011 | Weising |
| 2011/0275483 A1 | 11/2011 | Dugan et al. |
| 2012/0029666 A1 | 2/2012 | Crowley |
| 2012/0208676 A1 | 8/2012 | Shum et al. |
| 2012/0252580 A1 | 10/2012 | Dugan |
| 2012/0253487 A1 | 10/2012 | Dugan |
| 2012/0253489 A1 | 10/2012 | Dugan |
| 2012/0306643 A1 | 12/2012 | Dugan |
| 2013/0002435 A1 | 1/2013 | Utter, II |
| 2013/0006736 A1 | 1/2013 | Bethke et al. |
| 2013/0252731 A1 | 9/2013 | Dugan et al. |
| 2014/0011640 A1 | 1/2014 | Dugan |
| 2016/0263482 A1 | 9/2016 | Dugan |
| 2017/0080340 A1 | 3/2017 | Dugan |
| 2018/0117475 A1 | 5/2018 | Dugan |

FOREIGN PATENT DOCUMENTS

| | | |
|---|---|---|
| EP | 1 292 218 B1 | 4/2006 |
| EP | 1 702 560 | 9/2006 |
| EP | 1 743 571 A2 | 1/2007 |
| JP | 59-170173 | 9/1984 |
| JP | 08103568 | 4/1996 |
| WO | WO 96/05766 | 2/1996 |
| WO | WO 01/96986 A2 | 12/2001 |
| WO | WO 02/00111 | 1/2002 |
| WO | WO 02/078538 A2 | 10/2002 |
| WO | WO 03/015005 A2 | 2/2003 |
| WO | WO 2004/019172 A2 | 3/2004 |
| WO | WO 2004/032715 A2 | 4/2004 |
| WO | WO 2004/034221 A2 | 4/2004 |
| WO | WO 2005/016124 A2 | 2/2005 |
| WO | WO 2005/027720 A2 | 3/2005 |
| WO | WO 2005/029242 A2 | 3/2005 |
| WO | WO 2005/092177 | 10/2005 |

OTHER PUBLICATIONS

"Bluetooth." Wikipedia: The Free Encyclopedia. Aug. 10, 2009 <http://en.wikipedia.org/wiki/Bluetooth>.
lchinoseki-sekine et al., "Improving the Accuracy of Pedometer Used by the Elderly with the FFT Algorithm," Medicine & Science in Sports & Exercise 2006,1674-1681.
Mann, W. et al., "Smart Phones for the Elders: Boosting the Intelligence of Smart Homes," Am. Assoc. for Artificial Intell., (AAAI), Jul. 2002.
Office Action of U.S. Appl. No. 13/433,285 dated Feb. 8, 2013.
Jun. 10, 2013 Reply to Feb. 8, 2013 Office Action of U.S. Appl. No. 13/433,285.
Final Office Action of U.S. Appl. No. 13/433,285 dated Aug. 1, 2013.
Response to Final Office Action submitted with RCE of U.S. Appl. No. 13/433,285, filed Dec. 2, 2013.
Office Action of U.S. Appl. No. 13/440,987 dated Jun. 26, 2013.
Dec. 26, 2013 Reply to Jun. 26, 2013 Office Action of U.S. Appl. No. 13/440,987.
Final Office Action of U.S. Appl. No. 13/440,987 dated Feb. 12, 2014.
Examiner Interview Summary of U.S. Appl. No. 13/440,987 dated Feb. 25, 2014.
Office Action of U.S. Appl. No. 13/456,196 dated Nov. 6, 2012.
May 6, 2013 Reply to Nov. 6, 2012 Office Action of U.S. Appl. No. 13/456,196.
Final Office Action of U.S. Appl. No. 13/456,196 dated Aug. 29, 2013.
Response to Final Office Action submitted with RCE of U.S. Appl. No. 13/456,196, filed Dec. 30, 2013.
Examiner Interview Summary of U.S. Appl. No. 13/440,987 dated Mar. 6, 2014.
Amendment Submitted with After Final Consideration Pilot Program of U.S. Appl. No. 13/440,987, filed Apr. 14, 2014.
Advisory Action of U.S. Appl. No. 13/440,987 dated Apr. 22, 2014.
Supplemental Amendment of U.S. Appl. No. 13/440,987, filed May 14, 2014.
Non-Final Office Action of U.S. Appl. No. 13/433,285 dated Dec. 31, 2014.
Non-Final Office Action of U.S. Appl. No. 13/440,987 dated Jan. 29, 2015.
Applicant-Initiated Interview Summary of U.S. Appl. No. 13/433,285 dated Apr. 14, 2015.
Apr. 29, 2015 Reply to Jan. 29, 2015 Non-Final Office Action of U.S. Appl. No. 13/440,987.
Apr. 30, 2015 Reply to Dec. 31, 2014 Non-Final Office Action of U.S. Appl. No. 13/433,285.
Final Office Action of U.S. Appl. No. 13/440,987 dated May 19, 2015.
Final Office Action of U.S. Appl. No. 13/433,285 dated May 28, 2015.
Amendment After Notice of Appeal of U.S. Appl. No. 13/440,987, filed May 18, 2016.
Appeal Brief and Amendment After Notice of Appeal of U.S. Appl. No. 13/433,285, filed May 27, 2016.
Notice of Allowance of U.S. Appl. No. 13/440,987 dated Jun. 6, 2016.
Notice of Allowance of U.S. Appl. No. 13/433,285 dated Aug. 17, 2016.
Amendment after Notice of Allowance (Rule 312) of U.S. Appl. No. 13/440,987, filed Sep. 6, 2016.
Amendment After Allowance of U.S. Appl. No. 13/433,285, filed Nov. 17, 2016.
Non-Final Office Action of U.S. Appl. No. 15/364,241, dated Mar. 10, 2017.
Non-Final Office Action U.S. Appl. No. 15/159,664 dated Mar. 13, 2017.

(56) References Cited

OTHER PUBLICATIONS

Jul. 10, 2017 Reply to Mar. 10, 2017 Non-Final Office Action of U.S. Appl. No. 15/364,241.
Jul. 13, 2017 Reply and Terminal Disclaimer to Non-Final Office Action U.S. Appl. No. 15/159,664.
Notice of Allowance of U.S. Appl. No. 15/159,664 dated Sep. 13, 2017.
Examiner Interview and Submission of Terminal Disclaimer of U.S. Appl. No. 15/364,241, filed Oct. 4, 2017.
Notice of Allowance of U.S. Appl. No. 15/364,241 dated Nov. 1, 2017.
Comments on Examiners Statement of Reasons for Allowance of U.S. Appl. No. 15/364,241, filed Feb. 12, 2018.
Non-Final Office Action of U.S. Appl. No. 15/854,740 dated Oct. 4, 2018.
Feb. 5, 2019 Reply to Oct. 4, 2018 Non-Final Office Action of U.S. Appl. No. 15/854,740.
Notice of Allowance of U.S. Appl. No. 15/854,740 dated May 30, 2019.

* cited by examiner

SYSTEMS AND METHODS FOR FITNESS AND VIDEO GAMES

The present application is a continuation of and claims priority to U.S. patent application Ser. No. 15/364,241, filed Nov. 29, 2016 and titled "SYSTEMS AND METHODS FOR FITNESS AND VIDEO GAMES", which is a continuation of and claims priority to U.S. patent application Ser. No. 13/433,285, filed Mar. 28, 2012, now U.S. Pat. No. 9,533,228, and titled "SYSTEMS AND METHODS FOR FITNESS AND VIDEO GAMES", which claims priority to U.S. Provisional Patent Application No. 61/468,444 filed Mar. 28, 2011 and entitled "SYSTEMS AND METHODS FOR FITNESS AND VIDEO GAMES", and U.S. Provisional Patent Application No. 61/472,191 filed Apr. 5, 2011 and titled "SYSTEMS AND METHODS FOR FITNESS AND VIDEO GAMES,"each of which is hereby incorporated by reference herein in its entirety for all purposes.

FIELD OF THE INVENTION

The present application relates to fitness, and more particularly to systems and methods for fitness and video games.

BACKGROUND

Numerous applications for mobile phones, tablet computers or the like are available for tracking fitness and exercise. Examples include applications that track food consumed, provide work out routines or the like. Such applications continue to grow in popularity.

However, a need exists for mobile applications and systems that motivate an exerciser to continue exercising, exercise harder and have fun.

SUMMARY

In some aspects, a system is provided that includes (1) a plurality of mobile devices; and (2) an application on each mobile device, the application adapted to (a) allow exercisers to form an exercise group; (b) track position or change in position of each exerciser in the exerciser group; and (c) display an avatar having a position that is controlled by a position or change in position of one or more member of the exercise group.

In some aspects, a method for exercising using a mobile device is provided that includes providing an application on a first mobile device. The application adapted to (1) display an avatar on the first mobile device; (2) monitor exercise performed by a user of the first mobile device to obtain monitored exercise information; (3) communicate monitored exercise information from the first mobile device to one or more other mobile devices employed by one or more other users; (4) receive monitored exercise information from one or more other mobile devices employed by one or more other users; (5) display an avatar on the first mobile device; and (6) adjust a position of the avatar on the first mobile device based on monitored exercise information of the first user and monitored exercise information from one or more other mobile devices.

In some aspects, an application for a mobile device is provided that includes program code adapted to allow the mobile device to (1) display a video game have one or more avatars controllable by location information of a user of the mobile device and location information of at least one user of another mobile device; (2) share location information for the mobile device with at least one other mobile device; and (3) obtain location information of at least one other mobile device. Numerous other aspects are provided.

Other features and aspects of the present invention will become more fully apparent from the following detailed description, the appended claims, and the accompanying drawings.

DETAILED DESCRIPTION

Embodiments of the present invention provide systems and methods that motivate an exerciser to continue exercising, exercise harder and have fun during exercise. For example, in some embodiments, systems and methods are provided that allow an exerciser to employ a mobile phone, tablet or other similar portable computing device to join a group of exercisers in an exercising program.

Figure 1:
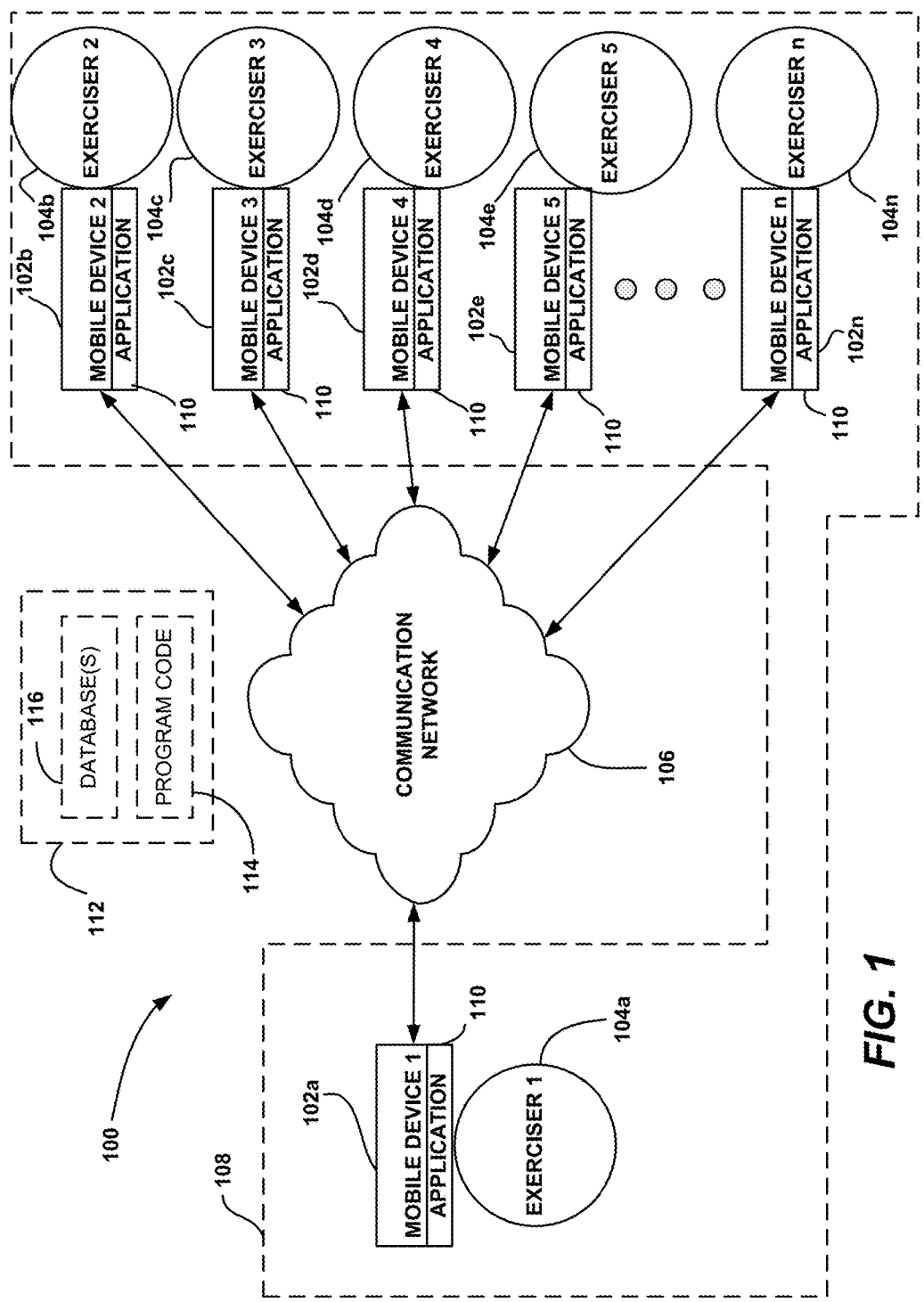
FIG. 1 illustrates a system for employing a mobile device to motivate an exerciser to exercise via communication with one or more other exercisers through one or more other mobile devices over a communication network in accordance with the present invention.

FIG. 1 illustrates a system 100 for employing a mobile device 102a to motivate an exerciser 104a to exercise via communication with one or more other exercisers 104b-n through one or more other mobile devices 102b-n over a communication network 106. The exercisers 104a-n may form an exercise group 108. Mobile devices 102a-n may include mobile (e.g., cellular) phones, other personal digital assistants (PDAs), tablet computers or the like which run an application 110 provided in accordance with the present invention and described further below. Exercisers 104a-n may be runners, cyclers, walkers or any other suitable exercisers. Communication network 106 may be the internet, one or more mobile telephone networks such as a 3G or 4G network, an intranet, a WiFi network or the like.

In one or more embodiments of the invention, each mobile device 102a-n may execute an application 110 that may:

(1) Employ GPS features of the mobile device to track position or change in position of the exerciser using the mobile device;
(2) Determine change in position information of the exerciser;
(3) Prompt the exerciser when and/or for how long the exerciser should change position;
(4) Determine speed information of the exerciser;

(5) Display a representation of the position, change in position, and/or speed of one or more exercisers on one or more of the mobile devices 102a-n;
(6) Communicate messages to one or more exercisers from one or more other exercisers;
(7) Monitor and/or communicate other biometric information of an exerciser such as heart rate, step rate, pulse, distance travelled, speed, etc.;
(8) Communicate position, change in position, heart rate, step rate, pulse, distance travelled, and/or other biometric information to one or more other exercisers, a third party such as family, friends, a doctor, an insurance company, a social network, etc.;
(9) Allow each exerciser to select an exercise group in which to participate; and/or
(10) Display information about the success of one or more exercisers and/or of the group at achieving a goal (e.g., time exercised, distance travelled, speed achieved, heart rate achieved, etc.).

In one particular embodiment, the application 110 may display information about and/or facilitate execution of a race in which each of the exercisers 104a-n may participate. For example, the race may be a relay race, a race between two destinations such as between two cities, across the island of Manhattan, across a state or the like, a race around the world, etc. Exerciser 104a (Exerciser 1) may be directed by mobile device 102a, such as by a visual and/or audio prompt, to exercise by walking, running, cycling or otherwise changing position for a predetermined time period and/or predetermined distance. In some embodiments, the application 110 may track the position of the exerciser 104a (exerciser 1) using a GPS feature of the mobile device 102a and communicate the position information to the exerciser 104a (exerciser 1) and/or to one or more of the mobile devices 102b-n of the exercisers 104b-n (and/or another third party if desired such as a family member, friends, retailers and/or restaurants near the exerciser, a social network site such as Facebook, Google+ or Twitter, etc. Each mobile device 102a-n may display a representation of the exerciser 104a's position (and/or change in position) as the exerciser 104a changes position. Other biometric information may be monitored, communicated and/or displayed such as heart rate, step rate, pulse rate, distance travelled, speed, etc.

Once the exerciser 104a (exerciser 1) completes his/her exercise such as by walking, running, cycling or otherwise changing position for the predetermined time period and/or predetermined distance, the second exerciser 104b (exerciser 2) may be begin exercising by walking, running, cycling or otherwise changing position for a predetermined time period and/or predetermined distance. In some embodiments, the application 110 may track the position of the exerciser 104b (exerciser 2) using a GPS feature of the mobile device 102b and communicate the position information to the exerciser 104b (exerciser 2) and/or to one or more of the mobile devices 102a, 102c-n of the exercisers 104a, 104c-n (exercisers 1, and 3-n). Each mobile device 102a-n may display a representation of the exerciser 104b's position (and/or change in position) as the exerciser 104b changes position. Other biometric information also may be monitored, communicated and/or displayed such as heart rate, step rate, pulse rate, etc. (In some embodiments, the periods in which exercisers exercise may overlap.)

The above process may repeat until each exerciser 104a-n has completed an exercise routine. For instance, each exerciser 104a-n may walk, run, cycle or otherwise change position one, two, three, etc., times during the race. Each exerciser 104a-n may exercise the same number or a different number of times during the race. While the above has been described with regard to exercisers changing position, it will be understood that other forms of exercise may be employed in which the exerciser does not change position significantly. For example, an exerciser may run or march in place, perform jumping jacks, etc., all of which may be detected by changes in acceleration measured by accelerometers within a mobile device such as a mobile phone, tablet computer, etc. Alternatively or additionally, heart rate, pulse or other biometric monitors may monitor and/or provide biometric information to a mobile device and track exercise.

Figure 2:
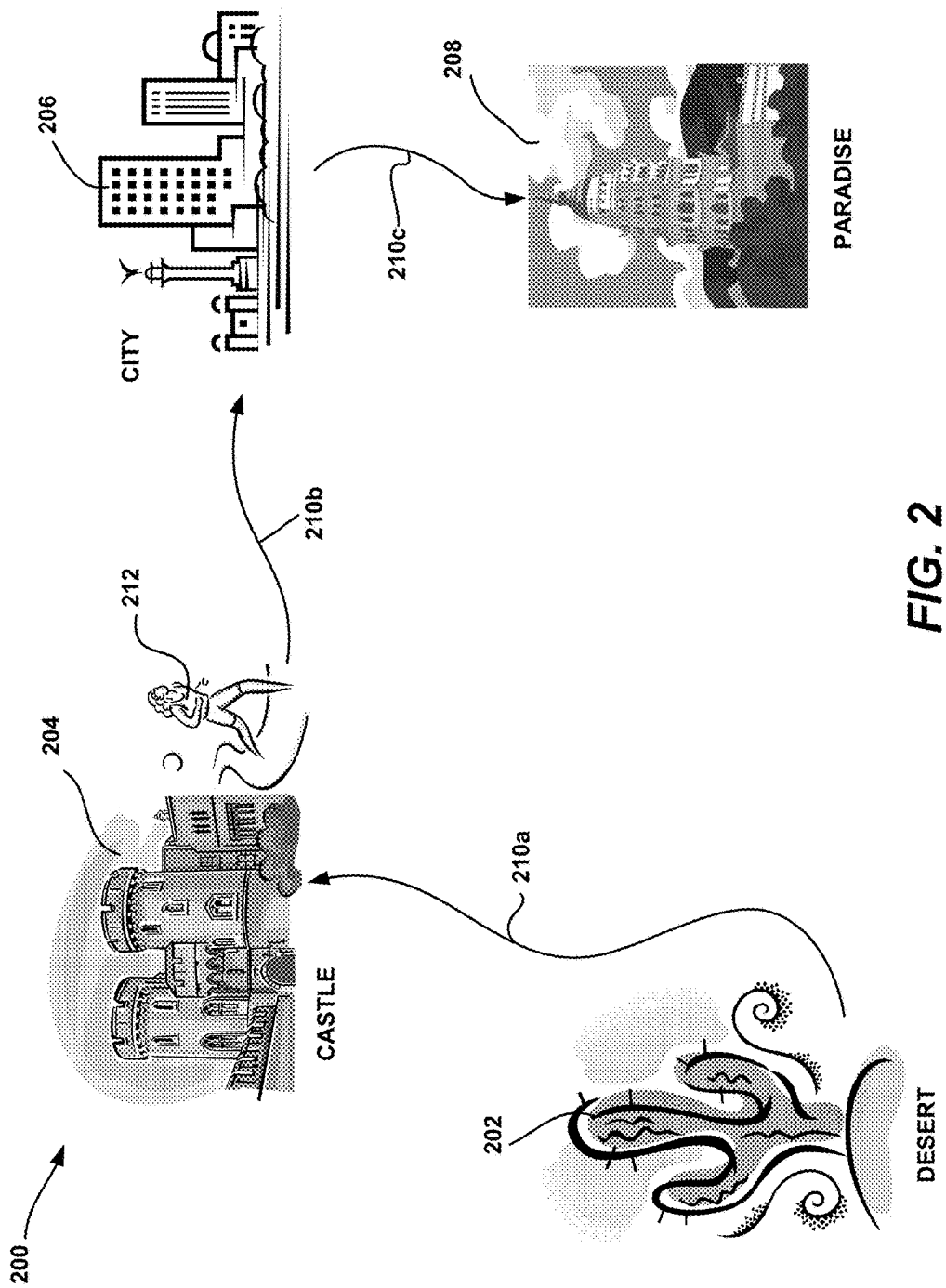
FIG. 2 is a schematic diagram of a first exemplary race in which a group may participate and which may be displayed on a mobile device in accordance with the present invention.

FIG. 2 is a schematic diagram of an exemplary race 200 in which the group 108 may participate and which may be displayed on each mobile device 102a-n using application 110. With reference to FIG. 2, the race 200 includes four destinations including a desert 202, a castle 204, a city 206 and paradise 208 that are connected by paths 210a-c, respectively. An avatar 212 is shown traversing path 210b between castle 204 and city 206. Fewer, more and/or different destinations may be employed.

In operation, race 200 may be displayed on each mobile device 102a-n via application 110 running on each mobile device 102a-n. In general, each mobile device 102a-n need not be running application 110 simultaneously and exercisers 104a-n may launch application 110 at any time on a respective mobile device 102a-n (or any other suitable device) to check the status of avatar 212 within the race 200. In some embodiments, the program code for managing and/or administering race 200 (or any video game as described below) may reside on a Web server or other server 112 (FIG. 1) in communication with the mobile devices 102a-n and/or may be managed and/or administered by a social networking site such as Facebook or Twitter. For example, web server 112 may include program code 114 and/or one or more databases 116 for managing and/or administering the race 200, storing information regarding exercisers 104a-n and/or their exercise activities, allowing new members to join the group 108, filtering potential new group members, etc. Likewise, race statistics may be displayed and/or viewed on such social networking sites.

With reference to FIGS. 1 and 2, the position of avatar 212 is controlled by the exercise (e.g., such as change in position, heart rate, steps taken, other biometric parameters, etc.) of exercisers 104a-n. For example, exerciser 104a (exerciser 1) may be directed by mobile device 102a, such as by a visual and/or audio prompt, to exercise by walking, running, cycling or otherwise changing position for a predetermined time period and/or predetermined distance. In some embodiments, the application 110 may track the position of the exerciser 104a (exerciser 1) using a GPS feature of the mobile device 102a and display a change in position of the avatar 212 in response to a change in position of exerciser 104a. In this manner the avatar 212 may travel along paths 210a-210c between the various destinations 202-208. Each mobile device 102a-n may display the avatar 212 changing position as the exerciser 104a changes position. Each exerciser 104a-n may be assigned a portion or "leg" of the race 200 to complete by moving a predetermined distance or for a predetermined time period. In some embodiments, the exercisers 104a-n may assist one another by offering encouragement, taking over the leg of the race 200 from another exerciser or the like. The avatar 212 may likewise change position based on biometric data measured for an exerciser such as heart rate, steps taken, pulse, etc.

Figure 3:
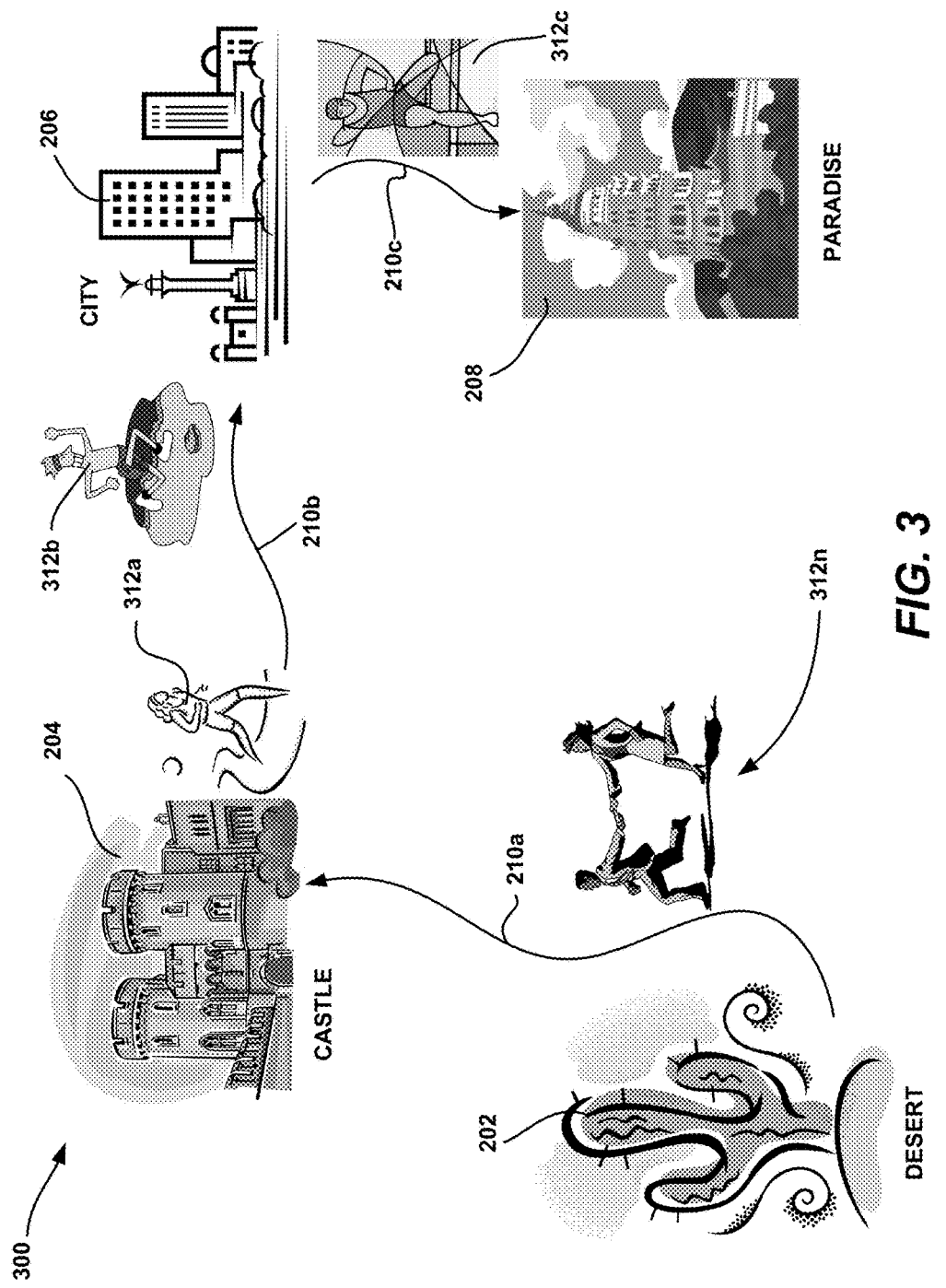
FIG. 3 is a schematic diagram of a second exemplary race in which a group may participate and which may be displayed on a mobile device in accordance with the present invention.

FIG. 3 is a schematic diagram of a race 300 in which multiple exercise groups 108 may compete with one another within the race 300. The race 300 is similar to the race 200, but includes a separate avatar 312a-n for each exercise group 108. In such embodiments, the mobile device of each exerciser in each group may be employed to display the race 300 and (multiple) avatar positions as the exercisers compete. Any number of exerciser groups may compete. In some embodiments, "handoffs" between exercisers within a group may be displayed as shown by avatar 312n which indicates that the current exerciser of an exercise group is ending his/her leg of the race and another member of the exercise group is beginning his/her leg of the race.

Exercisers within a group may not wish to share actual GPS coordinates with other members of their exercise group. Accordingly, in some embodiments, the application 110 may only communicate information representative of position or change in position of an exerciser to other mobile devices. For instance, when exerciser 104a begins his/her leg of a race, the application 110 on the mobile device 102a may treat the exerciser 104a as being at position x=0. Subsequent positions of the exerciser 104a may be adjusted accordingly so as to mask actual GPS coordinates of exerciser 104a. As mentioned, other biometric data such as heart rate, pulse rate, step rate, other parameters mentioned in Table 1 below, or the like may be monitored and employed to affect position, speed or the like of avatars 212 and/or 312a-n.

As stated, in some embodiments, the program code for managing and/or administering a race (or any video game as described below) may reside on a Web server or other server 112 in communication with the mobile devices 102a-n and/or may be managed and/or administered by a social networking site such as Facebook or Twitter. In addition to races, other competitive sports activities may include a "virtual" baseball or kickball game in which accelerometers within a mobile device are used to detect a kick, jump, swing of a baseball bat (or arm/hand that mimics a swing of a baseball bat), swing of a tennis racquet, or the like. For example, with reference to FIG. 4, an exercise group 108 may participate in a virtual baseball game 400 in which each exerciser 104a-n in the group 108 is assigned a position with an avatar 412a-n that is displayed in that position on a virtual baseball field 414 displayed on each mobile device 102a-n. In some embodiments, a remote web server, such as web server 112 in FIG. 1, may be programmed to communicate with the mobile device of each exerciser 104a-n, host the virtual game, issue avatar position updates to each mobile device used by an exerciser 104a-n (e.g., based on biometric or other information received from each mobile device as described below).

Figure 4:
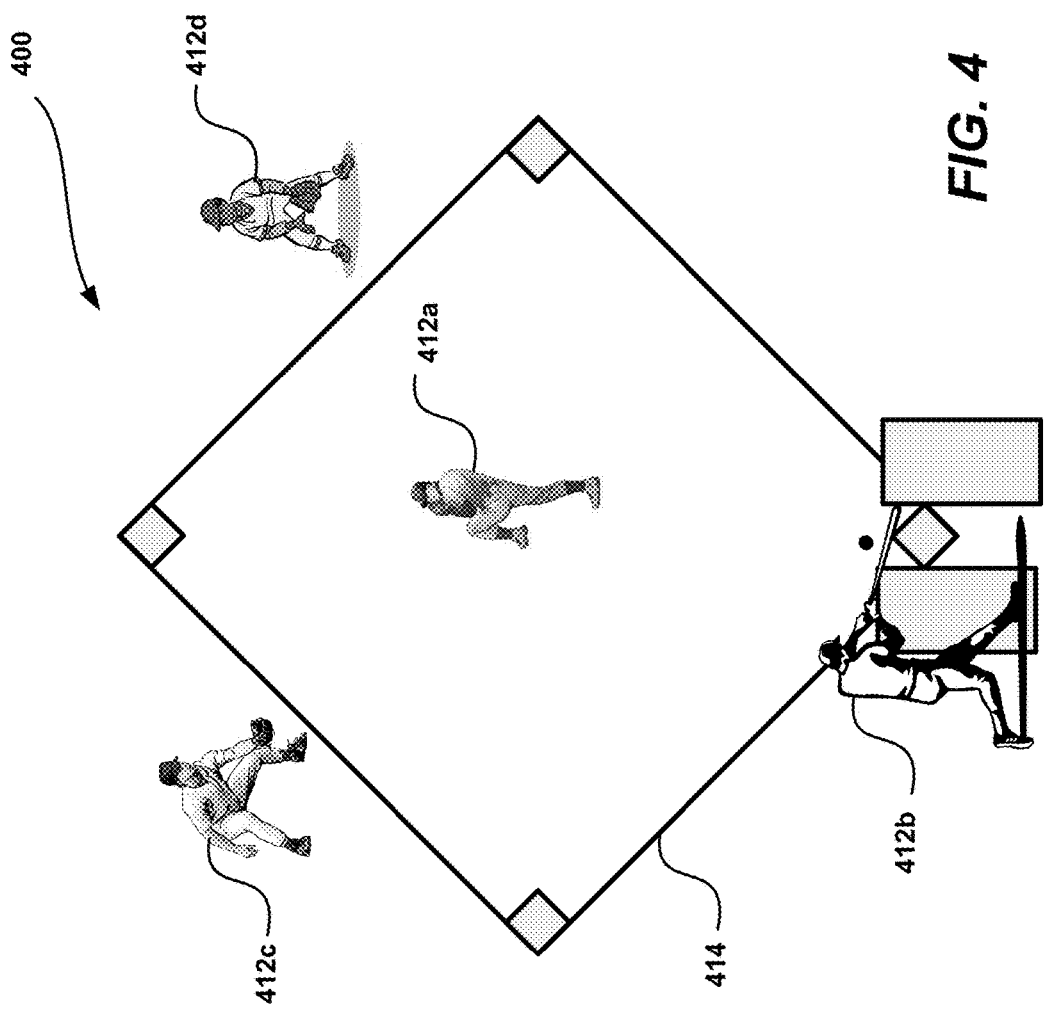
FIG. 4 is an exemplary baseball game in which a group may participate and which may be displayed on a mobile device in accordance with the present invention.

During a game, the position and/or behavior of each avatar 412a-d on a baseball field 414 may be controlled by the GPS location and/or other data measured by each mobile device 102a-n (and/or by biometric data collected by the mobile device 102a-n such as heart rate, speed, cadence, pulse, etc.). For example, exerciser 1 (represented by avatar 412a) may pitch a ball to exerciser 2 (represented by avatar 412b) by pretending to pitch a ball with his/her mobile device. For instance, exerciser 1 (represented by avatar 412a) may hold his/her mobile device in his/her pitching arm, and carry out a pitching motion while holding the mobile device. Accelerometers within the mobile device may measure forces generated during the pitch, for example, by measuring x, y and/or z axis acceleration. Each mobile device 102a-n may display an avatar representative of exerciser 1 pitching a ball and/or ball speed in the "virtual" game may be based on the real world pitch of exerciser 1 (e.g., as measured by accelerometers in the mobile device of exerciser 1, one or more external accelerometers in communication with the mobile device of exerciser 1 such as an accelerometer mounted in a write band, or the like). Exerciser 2 (represented by avatar 412b) may hit the ball pitched by exerciser 1 (represented by avatar 412a) by swinging his/her mobile device at the appropriate time based on the pitch of exerciser 1 (represented by avatar 412a) or by performing some predetermined exercise requirement (e.g., running for a predetermined time, distance and/or speed, maintaining a predetermined heart rate range for a predetermined time, or the like). Assuming exerciser 2 (represented by avatar 412b) actually hits the virtual ball (e.g., swings his/her mobile device at the correct time or performs a predetermined exercise requirement), each mobile device 102a-n may display a ball being hit by the avatar 412b of exerciser 2. Exerciser 3 (represented by avatar 412c), who may be playing infield or outfield, may catch the ball hit by exerciser 2 by running or performing some other predetermined exercise so as to cause his/her avatar 412c to run toward the virtual ball hit by the avatar 412b of exerciser 2. Exerciser 3 may "catch" the ball hit by exerciser 2 using his/her mobile device, for example. In general, all types of ball play may be similarly conducted using the accelerometers and/or GPS features of mobile devices 102a-n (or external biometric measurement devices that provide biometric information to the mobile devices). Other virtual games may be similarly played such as tennis football, basketball, hockey, volleyball, or the like. While only four avatars are shown in FIG. 4 representing four exercisers, it will be understood that fewer or more exercisers and/or avatars may be employed.

Note that virtual game play may or may not be performed in real time. In some embodiments, the position or other characteristics of an avatar may be changed during or after exercise is performed.

In one or more embodiments, an exercise group, such as a group of friends, a group with members that share certain characteristics such as similar age, interests, historical exercise performance, education, or the like (which in some embodiments may be identified via a social networking site), may agree to play a virtual game while each group member works out. For instance, one group member may wish to work out at a local gym, while another may wish to work out in his/her home, etc. As described above, each gaming device such as a cellular telephone, tablet computer, etc., may include an application which displays a video game in which each group member may control one or more aspects of the video game. For instance, each group member's exercise may control the position, speed, movement or the like of a video game character. In this manner a group of friends may be motivated to work out together. Similarly, an exerciser may enter a "pick up" game with previously unknown exercisers. In a further example, such games may be used in a match-making embodiment (e.g., to introduce people with similar interests and/or geographic location that meet predetermined criteria such as age, education, marital status, or the like). For example, a first exerciser may be at a local health club and wish to meet another exerciser within the health club. He/she may send out a request for someone within the health club to participate and/or compete in a video game or virtual competition. In some embodiments, an application on a mobile device may be used to access a social networking cite to identify exercise partners. For instance, the health club may maintain a Facebook or similar page that may be used to identify exercisers currently at the health club that may wish to interact, such as train or compete, with other exercisers at the health club. The request may include filters such as required characteristics of the invited exerciser (e.g., female, single, age, employment status, etc.). Accordingly, an application with such functionality may be provided to execute on a mobile device or other gaming device of the exercisers. Any suitable biometric information may be monitored during exercise such as position, speed, heart rate, cadence, etc.

Figure 5:
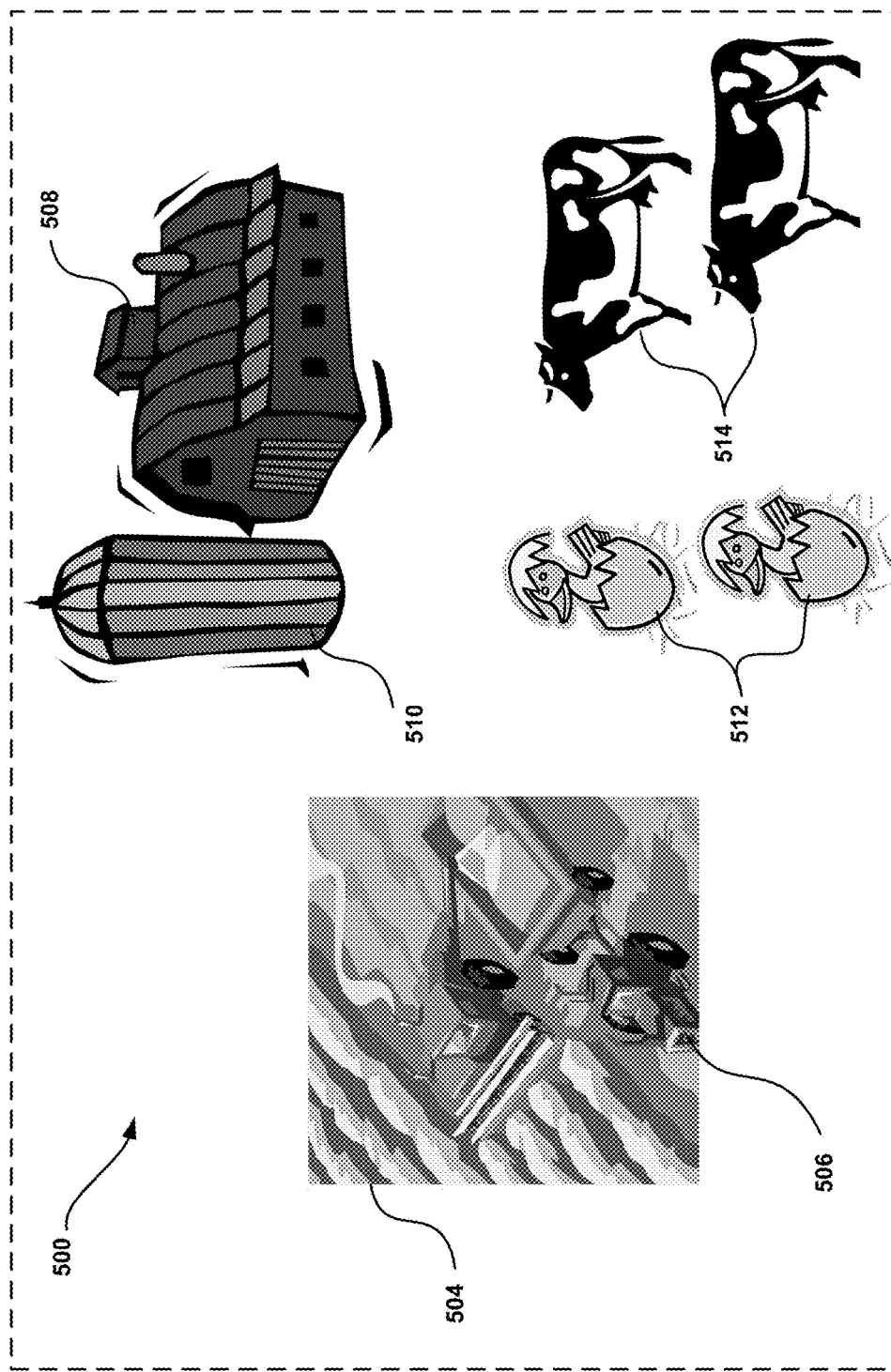
FIG. 5 is an exemplary social network game in which a group may participate and which may be displayed on a mobile device in accordance with the present invention.

FIG. 5 is a schematic diagram of an exemplary video game 500 for use by mobile devices 102*a-n* via a Web server or other server 112 in communication with the mobile devices 102*a-n* and/or may be managed and/or administered by a social networking site such as Facebook, Google+ or Twitter. In the embodiment of FIG. 5, a virtual farm 502 is provided that includes crops 504, a tractor 506, a barn 508, a silo 510, chickens 512, cows 514 and/or any other typical farm items (not shown). In some embodiments, the goal of such a video game 500 may be to grow more crops, buy more land, obtain more eggs, chickens, cows or milk, plow fields, harvest crops, or the like. In accordance with embodiments of the present invention, performance of such activities may be enhanced by exercise of one or more exercisers 104*a-n*. For instance, if exerciser 104*a* is playing the video game 500, exerciser 104*a* may be assigned (or establish) an exercise goal such as a number of miles to walk or run, a number of minutes to walk or run on a treadmill, a length of time to perform an aerobics routine, a number of jumping jacks to perform, etc. Completion of such goals may be monitored by a mobile device 102*a-n* as previously described (e.g., through use of accelerometers of the mobile device or external accelerometers, GPS-features, use of heart rate monitors, verification by a third party such as a friend or health club staff, etc.). In exchange for completion (or partial completion) of the exercise goal, an exerciser may be rewarded with more land, more or heartier crops, more cows or more milk production from cows, new farm animals or equipment, gas or diesel fuel for farm equipment, more grain in the silo 510, more tokens or virtual money for farm item purchases, or the like.

In some embodiments, an exercise group 108 may be assigned to a farm (e.g., a community farm). Exercisers 104*a-n* within the exercise group 108 may be assigned farm tasks that are enhance by exercise as described above. Being a part of such a group may be provide additional motivation for each exerciser 104*a-n* to complete regular exercise (e.g., due to peer pressure).

Other Embodiments

The exercisers 104*a-n* may wish to have a more interactive experience. Accordingly, in some embodiments, the race 200 and/or 300 may be part of a video game in which the avatar 212 and/or avatars 312*a-n* encounter monsters, snipers, assassins, wild animals, obstacles or other typical video game scenarios that the avatar(s) must navigate through and/or survive. In this regard, if exerciser 104*a* is currently exercising, his/her exercise level may directly affect video game play of either the exerciser 104*a* or of the other exercisers 104*b-n*. For instance, exercise of exerciser 104*a* may be employed to affect the speed, striking force, game level, etc., of the avatar 212. Exemplary video game character performance levels that may be affected by a measured exercise parameter are shown below in Table 1. Such parameters may be measured using suitable sensors such heart rate monitor chest straps, pedometers, accelerometers, or the like.

TABLE 1

| MONITORED EXERCISER PERFORMANCE LEVEL | VIDEO GAME CHARACTER PERFORMANCE LEVEL CONTROLLED |
|---|---|
| pedaling rate | speed, striking force |
| stepping rate | speed, striking force |
| rowing rate | speed, striking force |
| running rate | speed, striking force |
| pulse rate | speed, energy level, accuracy |
| striking force | striking force |
| swing velocity | swing velocity |
| distance traveled | game level |
| time exercised | game level |

In one example, exercise of exerciser 104*a* may be used to control speed, striking force or game level of a video game in which avatar 212 is a character. One or more of the other exercisers 104*b-n* in group 108 may control other parameters of the avatar 212 such as movement to the right, left, up, down, other movements such as jumping, kicking, firing a weapon, steering a car, etc. For instance, while exercising, the exerciser 104*a* may not be free to use his/her hands to manipulate the mobile device 102*a* in a manner that would cause the avatar 212 to turn right or left, kick, jump, fire a weapon, etc. Nonetheless, the exercise of the exerciser 104*a* may be used to affect the speed, striking force, game level, etc., of the avatar 212. One or more of the other exercisers 104*b-n* in group 108 who is/are not exercising may use his/her respective mobile device 102*b-n* to cause movement of the avatar 212 to the right or left, to kick, etc., or otherwise proceed through the video game (e.g., using accelerometers within the mobile device, tapping the screen of the mobile device, etc.) while the exerciser 104*a* is exercising.

Figure 6:
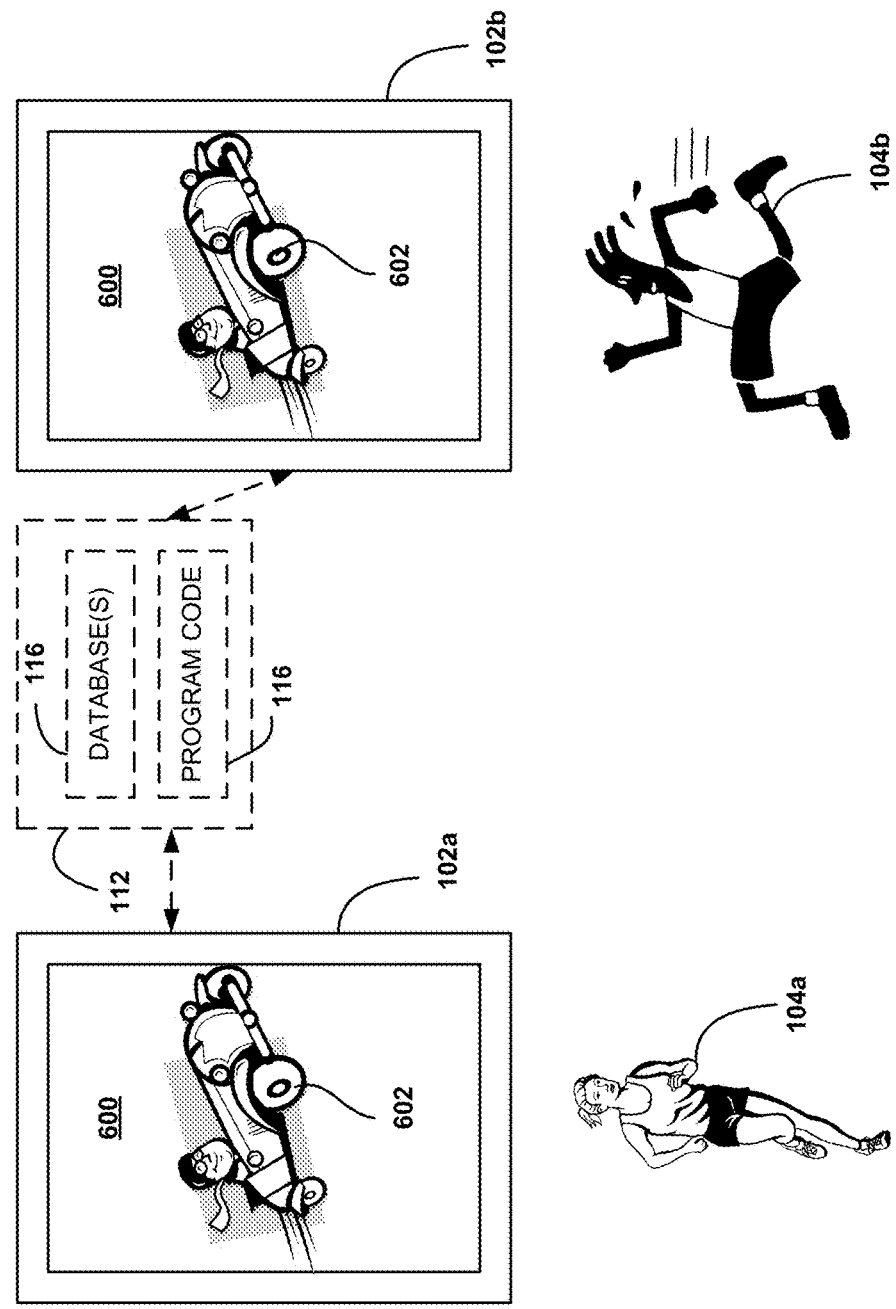
FIG. 6 is an exemplary car race in which a group may participate and which may be displayed on a mobile device in accordance with the present invention.

In some embodiments, primary control of the avatar 212 may pass back and forth between two or more members of an exercise group over and over during a work out routine (e.g., as the person exercising changes). For example, FIG. 6 is a schematic diagram of a video game 600 executing on mobile devices 102*a* and 102*b* of exercisers 104*a* and 104*b*, respectively. Other numbers of mobile devices and/or exercisers may be used.

Mobile devices 102*a-b* include an application for the video game 600. In the example shown, a race car 602 is shown. Any other video game type, character, setting or the like may be used (as described above, for example). Mobile devices 102*a-b* may communicate with each other directly, such as via WIFI, a cellular network, some other protocol, etc., or may communicate indirectly through a web server 112 or similar system. In the embodiment shown, control of the steering and/or braking of car 602 is controlled by the exerciser 102*a* or 102*b* who is not exercising, while control the speed of the car 602 is controlled by the exerciser 102*a* or 102*b* who is exercising. Who exercises when and/or for how long may be determined by the exercisers 102*a*, 102*b*, a third party such as other members of an exercise group, a trainer, a retailer that may offer rewards for completing an exercise program, or the like. For instance, in some embodiments, web server 112 may host a web interface in which the race 600, or information or statistics about the race 600, may be observed. Through such a web interface, an exerciser or other party may enter a desired exercise duration for the game 600, when and/or for how long each exerciser will exercise, etc. Such information may be communicated to the mobile devices 102*a-n* before and/or during game play, for example.

In other embodiments, the exerciser 104*a* may control such movements of an avatar as well. In one particular embodiment, an application 110 may be adapted to process voice commands of the exerciser 104a to control movement or other behaviors of an avatar. Exemplary voice commands are shown in Table 2 below.

TABLE 2

| VOICE COMMAND OF EXERCISER | VIDEO GAME CHARACTER CHARACTERISTIC CONTROLLED |
|---|---|
| "L" or "Left" | turn left |
| "R" or "Right" | turn right |
| "J" or "Jump" | jump |
| "D" or "Duck" | duck or drop to the ground |
| "B" or "Back" | move back |
| "K" or "Kick" | kick |
| "F" or "Fly" | fly |

In other embodiments, another sound of exerciser 104a may be used to control the avatar, such as a "clacking" sound. For instance, the exerciser 104a may clack his/her tongue once to turn right, twice to turn left, thrice to jump, etc., similar to Morse code. In some embodiments, the exerciser 104a may select/record sounds that are to be interpreted by the application 110 to correspond to turning left or right, jumping, ducking, kicking with a left or right leg, flying, etc.
Additional Embodiments In some embodiments, a gaming device such as a mobile telephone, tablet computer, or the like, may include a video game with characteristics that change based on the number of other gaming devices near the gaming device. For example, an application may be provided for execution on mobile devices. The application may monitor whether mobile devices are within a predetermined geographic area of one another, such as by using GPS location information from each mobile device. Characteristics of a video game running on one or more of the mobile devices may depend on or otherwise be affected by the number or proximity of other mobile devices (e.g., video game characteristics such as the number or position of video game characters within the video game, the landscape or background characteristics of the video game, etc.). In some embodiments, biometric information collected by each mobile device such as heart rate, speed, etc., similarly may be used to affect the video game by affecting the speed, strength, position, etc., of characters within the video game). Further, in some embodiments, certain game levels, movements, etc., may only be possible within the video game if a large enough (or small enough) number of mobile devices are present within a predetermined location.

In some embodiments, the video game may communicate with a social networking site such as Facebook, Google+ or Twitter, and such social networking sites may identify or notify friends or affiliated groups of the presence of friends or members within a particular geographic area (e.g., using GPS features of mobile devices). Such friends or affiliated groups may be prompted to participate in video games or to otherwise interact.

In one or more embodiments, video game characteristics of a video game may be affected by location information of the mobile device executing the video game. For instance, a user may only enter a certain game level if he/she is physically located at a particular location such as a restaurant, a mall, a computer store, a city, a monument, or the like. The user's position may be determined, for example, using GPS features of the mobile device.

In yet other embodiments, location information from mobile devices may be collected and/or aggregated to track position, travel habits, etc., of a group of people such as lawyers, doctors, gamers, etc., that are members of a social network. In fact, a virtual world or map may be generated by tracking the position of one or mobile devices during any given time period. In some embodiments, such information may be used to affect video game characteristics such as game environment, number of video game characters, or the like.

The foregoing description discloses only exemplary embodiments of the invention; modifications of the above disclosed apparatus and method which fall within the scope of the invention will be readily apparent to those of ordinary skill in the art. For instance, any number of performance levels of an exerciser may be monitored and used to control any number of performance levels of a video game character. Further, old video games may be modified for use with the present invention, or new video games may be developed.

In some embodiments, exercisers may join exercise groups via a social networking site such as Facebook, Google+ or Twitter. Such social networking sites may collect information on the exercisers and make recommendations for exercise groups based on age, weight, type of exercise, geographic location or the like.

In some embodiments, exercisers training for a marathon or other exercise goal may be identified by a social networking site (e.g., based on hobbies, interests, or other identifying data posted by the exerciser on the social networking site). One or more exercisers, or the social networking site itself, may invite like exercisers to join a training group. In some embodiments, retail businesses such as clothing stores, restaurants, cellular telephone providers, or the like, may offer members of the group discounts such as reduced rate clothing, discounted meals, reduced cell phone rates or free minutes (e.g., for calls between group members) or the like.

In some aspects, a method for exercising using a mobile device is provided that includes providing an application on a first mobile device. The application adapted to (1) display an avatar on the first mobile device; (2) monitor exercise performed by a user of the first mobile device to obtain monitored exercise information; (3) communicate monitored exercise information from the first mobile device to one or more other mobile devices employed by one or more other users; (4) receive monitored exercise information from one or more other mobile devices employed by one or more other users; (5) display an avatar on the first mobile device; and (6) adjust a position of the avatar on the first mobile device based on monitored exercise information of the first user and monitored exercise information from one or more other mobile devices. The monitored exercise information may exchanged between mobile devices via a remote web server, such via a social network web site running on the remote web server.

In some aspects, an application for a mobile device is provided that includes program code adapted to allow the mobile device to (1) display a video game have one or more avatars controllable by location information of a user of the mobile device and location information of at least one user of another mobile device; (2) share location information for the mobile device with at least one other mobile device; and (3) obtain location information of at least one other mobile device. In some embodiments, the program code may be adapted to allow a user of the mobile device to join an exercise group; and communicate location information for the mobile device with mobile devices of other members of the exercise group. In some embodiments, the program code may be adapted to communicate with mobile devices of other members of the exercise group through a social network web site. In additional embodiments, the program code may be adapted to switch control of motion of the avatar on the mobile device between the user of the mobile device and a user of another mobile device.

Accordingly, while the present invention has been disclosed in connection with exemplary embodiments thereof, it should be understood that other embodiments may fall within the spirit and scope of the invention, as defined by the following claims.

The invention claimed is:

1. A system for cooperative control of a video game avatar, the system comprising:
 a plurality of mobile devices, each mobile device being with a different one of a plurality of users; and
 computer program code stored in each of the plurality of mobile devices;
 wherein the computer program code stored in a first mobile device of the plurality of mobile devices, when executed by the first mobile device, causes the first mobile device to:
  direct a user of the first mobile device to perform an exercise movement;
  measure, by sensors communicatively coupled to the first mobile device, exercise parameters of the user of the first mobile device;
  transmit, by communications facilities of the first mobile device, the measured exercise parameters of the user to a server, and receive measured exercise parameters of other users;
  execute a video game on the first mobile device, the video game operable to employ the measured exercise parameters of the users to cooperatively control movement of an avatar within the video game;
  transmit location information of the user to the server and to receive location information of other users, wherein the video game has one or more avatars controllable based on location information of the user of the first mobile device and location information of other users,
  wherein a first movement parameter of the avatar is controlled based upon a first exercise parameter of a first user and a second movement parameter of the avatar is controlled based upon a second exercise parameter of a second user, and
  wherein movement capabilities of the video game avatar for playing the video game are set based upon an exercise performance level of the users.

2. The system of claim 1, wherein the computer program code stored in the first mobile device, when executed by the first mobile device, causes the first mobile device to output images to a display of the first mobile device depicting a movement of the avatar, which is representative of the exercise movement of the user of the first mobile device.

3. The system of claim 1, wherein the computer program code stored in the first mobile device, when executed by the first mobile device, further causes the first mobile device to direct the first user to perform a first exercise for a first period of time and then direct the first user to perform a second exercise for a second period of time.

4. The system of claim 1, wherein the communications facilities of the first mobile device to allow the user to join an exercise group of other users.

5. The system of claim 4, wherein the computer program code, when executed by the first mobile device, causes the first mobile device to: communicate location information for the user to other users within the exercise group.

6. The system of claim 4, wherein the computer program code stored in the first mobile device, when executed by the first mobile device, causes the first mobile device to display information associated with achievement of a goal of the exercise group.

7. The system of claim 4, wherein competitiveness in the video game is based upon the exercise group achieving a goal of the exercise group.

8. The system of claim 4, wherein the computer program code, when executed by the first mobile device, causes the first mobile device to communicate with other users within the exercise group through a social network web site.

9. The system of claim 1, wherein the computer program code stored in the first mobile device, when executed by the first mobile device, causes the first mobile device to prompt other users to exercise for a predefined amount of time.

10. The system of claim 1, wherein the computer program code stored in the first mobile device, when executed by the first mobile device, causes the first mobile device to prompt the user when to perform exercise.

11. The system of claim 1, wherein the computer program code stored in the first mobile device, when executed by the first mobile device, causes the first mobile device to communicate messages to the other users.

12. A system for cooperative control of a video game avatar, the system comprising:
 a plurality of mobile devices, each mobile device being with a different one of a plurality of users; and
 computer program code stored in each of the plurality of mobile devices;
 wherein the computer program code stored in a first mobile device of the plurality of mobile devices, when executed by the first mobile device, causes the first mobile device to:
  direct a user of the first mobile device to perform an exercise movement;
  measure, by sensors coupled to the first mobile device, exercise parameters of the user of the first mobile device;
  transmit, by communications facilities of the first mobile device, the measured exercise parameters of the user to a server, and receive measured exercise parameters of other users;
  execute a video game on the first mobile device, the video game operable to employ the measured exercise parameters of the users to cooperatively control movement of an avatar within the video game,
  wherein a first movement parameter of the avatar is controlled based upon a first exercise parameter of a first user and a second movement parameter of the avatar is controlled based upon a second exercise parameter of a second user, and
  wherein movement capabilities of the video game avatar for playing the video game are set based upon an exercise performance level of the users; wherein the video game is further operable to switch which movement parameter of the avatar is controlled based upon the exercise parameters of the users such that the first movement parameter of the avatar is controlled based upon the second exercise parameter of the second user and the second movement parameter of the avatar is controlled based upon the first exercise parameter of the first user.

13. A system for cooperative control of a video game avatar, the system comprising:

a plurality of mobile devices, each mobile device being with a different one of a plurality of users; and computer program code stored in each of the plurality of mobile devices;

wherein the computer program code stored in a first mobile device of the plurality of mobile devices, when executed by the first mobile device, causes the first mobile device to:

direct a user of the first mobile device to perform an exercise movement;

measure, by sensors communicatively coupled to the first mobile device, exercise parameters of the user of the first mobile device;

transmit, by communications facilities of the first mobile device, the measured exercise parameters of the user to a server, and receive measured exercise parameters of other users; and execute a video game on the first mobile device, the video game operable to employ the measured exercise parameters of the users to cooperatively control movement of an avatar within the video game, wherein a first movement parameter of the avatar is controlled based upon a first exercise parameter of a first user and a second movement parameter of the avatar is controlled based upon a second exercise parameter of a second user, and wherein movement capabilities of the video game avatar for playing the video game are set based upon an exercise performance level of the users, wherein the computer program code stored in the first mobile device, when executed by the first mobile device, causes the first mobile device to communicate measured biometric information of the user to a third party.

14. A method for cooperative control of a video game avatar, the method comprising:

providing a plurality of mobile devices, each mobile device of the plurality of mobile devices being with a different user; and providing computer program code stored in each of the plurality of mobile devices, wherein execution of the computer program code stored in a first mobile device of the plurality of mobile devices by the first mobile device, causes the first mobile device to:

direct a user of the first mobile device to perform an exercise movement;

measure, by sensors communicatively coupled to the first mobile device, exercise parameters of the user of the first mobile device;

transmit the measured exercise parameters of the user to a server, and receive measured exercise parameters of other users; and execute a video game on the first mobile device, the video game operable to employ the measured exercise parameters of the users to cooperatively control movement of an avatar within the video game;

transmit location information of the user to the server and receive location information of other users, wherein the video game has one or more avatars controllable based on location information of the user of the first mobile device and location information of other users, wherein a first movement parameter of the avatar is controlled based upon a first exercise parameter of a first user and a second movement parameter of the avatar is controlled based upon a second exercise parameter of a second user, and wherein movement capabilities of the video game avatar for playing the video game are set based upon an exercise performance level of the users.

15. The method of claim 14, further comprising transmitting location information of a user to the server and receiving location information of other users.

16. The method of claim 14, further comprising controlling one or more avatars of the video game based, at least in part, on location information of a user and location information of other users.

17. The method of claim 14, wherein the computer program code stored in the first mobile device, when executed by the first mobile device, further causes the first mobile device to allow a user to join an exercise group of other users.

18. The method of claim 17, further comprising communicating location information for the user to other users within the exercise group.

* * * * *